United States Patent [19]

Green et al.

[11] 4,096,199
[45] Jun. 20, 1978

[54] PROCESS FOR REGENERATING FLUOROSULFURIC ACID CATALYST

[75] Inventors: Donald L. Green; William C. Behrmann; David E. Allan, all of Baton Rouge, La.

[73] Assignee: Exxon Research & Engineering Co., Linden, N.J.

[21] Appl. No.: 772,636

[22] Filed: Feb. 28, 1977

[51] Int. Cl.² ............................................. C07C 3/54
[52] U.S. Cl. ........................ 260/683.47; 260/683.58; 252/411 R
[58] Field of Search ...................... 260/683.48, 683.47, 260/683.58, 683.51; 252/411 R; 208/13

[56] References Cited

U.S. PATENT DOCUMENTS

| | | | |
|---|---|---|---|
| 2,965,558 | 12/1960 | Brant | 208/13 |
| 3,887,635 | 6/1975 | Parker et al. | 260/683.47 |
| 3,925,318 | 12/1975 | Parker et al. | 260/683.58 |

Primary Examiner—George Crasanakis
Attorney, Agent, or Firm—John W. Ditsler

[57] ABSTRACT

A process for regenerating an alkylation catalyst comprising fluorosulfuric acid, said catalyst being at least partially deactivated, which comprises:

(1) contacting at least a portion of the fluorosulfuric acid with water to form an acid-water mixture, thereby converting at least a portion of the fluorosulfuric acid therein to hydrogen fluoride and sulfuric acid;

(2) removing at least a portion of the hydrogen fluoride from said acid-water mixture formed in step (1) by contacting same with a stripping agent to form a gaseous phase containing hydrogen fluoride and said stripping agent and a liquid phase containing sulfuric acid and sludge;

(3) cooling the gas phase formed in step (2) to a temperature sufficient to form a mixed phase comprising at least a liquid phase containing hydrogen fluoride; and (4) treating the mixed phase formed in step (3) with sulfur trioxide under substantially liquid phase conditions so as to regenerate the fluorosulfuric acid. In a preferred embodiment, at least a portion of the regenerated fluorosulfuric acid is recycled to the alkylation zone for use as an alkylation catalyst therein.

22 Claims, 3 Drawing Figures

PROCESS FOR REGENERATING FLUOROSULFURIC ACID CATALYST

BACKGROUND OF THE INVENTION

1. Field of the Invention

The present invention relates to a process for regenerating a catalyst of the type used in hydrocarbon conversion processes. More particularly, this invention relates to a process for regenerating a catalyst comprising fluorosulfuric acid, at least a portion of said catalyst having become deactivated due to the formation of diluents during contact with a hydrocarbon feedstock in an alkylation process.

2. Description of the Prior Art

It is well known in the prior art that as the alkylation reaction proceeds, an organic material will form and will accumulate in the fluorosulfuric acid catalyst phase. The material has been given a variety of names including red oil, sludge, organic sludge, acid oil and the like. This organic material is a by-product of acid-catalyzed hydrocarbon reactions such as occur during alkylation and has been described in the literature comprising primarily a conjunct polymer (such as is described in Miron, S. and Lee, R. J., "Molecular Structure of Conjugated Polymers", J. Chem Eng. Data, Vol. 8, p. 150–160 (1963), the disclosures of which are incorporated herein by reference). These conjunct polymers are complex mixtures of olefinic, conjugated cyclic hydrocarbons that may be formed from any type of hydrocarbon except aromatics. More specifically, they are believed to be cyclic polyolefinic hydrocarbons with a high proportion of conjugated double bonds, no two of which are in the same ring. Five membered ring systems predominate, but larger, and possibly also smaller, rings are believed to be present. The accumulation of this conjunct polymer and any other acid diluents will ultimately cause the activity of fluorosulfuric acid catalysts to decline until said catalysts cease to exhibit economic activity. In such cases, depending upon economic factors, the catalyst may be replaced or regenerated to restore desired activity levels.

One method for regenerating catalysts comprising fluorosulfuric acid has been suggested in U.S. Pat. No. 3,766,293, the disclosures of which are incorporated herein by reference. According to this method, an alkylation catalyst comprising fluorosulfuric acid that is at least partially deactivated may be regenerated by (1) contacting said catalyst with water so as to convert at least a portion of the fluorosulfuric acid to hydrogen fluoride and sulfuric acid; (2) removing at least a portion of the hydrogen fluoride from said catalyst by contacting the same with a paraffin so as to form a hydrocarbon phase containing hydrogen fluoride; and (3) treating said hydrocarbon phase with sulfur trioxide to regenerate the fluorosulfuric acid. While this method is effective in regenerating said catalyst, it is believed that the particular regeneration technique described herein below has certain advantages over that disclosed in U.S. Pat. No. 3,766,293 which heretofore have not been disclosed.

SUMMARY OF THE INVENTION

Now according to the present invention, an improved process for regenerating a deactivated or partially deactivated alkylation catalyst comprising fluorosulfuric acid has been discovered, said deactivated or partially deactivated catalyst containing an organic sludge formed during said alkylation process, which comprises the steps of:

(1) contacting at least a portion of the fluorosulfuric acid with water to form an acid-water mixture, thereby converting at least a portion of the fluorosulfuric acid contained therein to hydrogen fluoride and sulfuric acid;

(2) removing at least a portion of the hydrogen fluoride from said acid-water mixture formed in step (1) by contacting same with a stripping agent to form a gaseous phase containing hydrogen fluoride, fluorosulfuric acid and stripping agent and a liquid phase containing sulfuric acid and sludge;

(3) cooling the gaseous phase formed in step (2) to a temperature sufficient to form a mixed phase comprising at least a liquid phase containing hydrogen fluoride; and (4) treating the mixed phase formed in step (3) with sulfur trioxide at a temperature sufficient to maintain substantially liquid phase conditions so as to regenerate the fluorosulfuric acid.

The present invention represents an improvement over the process described in U.S. Pat. No. 3,766,293 in that, in one embodiment thereof, it is recognized that fouling and undesirable side reactions due to the use of saturated hydrocarbons as a stripping agent can be minimized by effecting various steps in the fluorosulfuric acid regeneration at different temperature conditions. For this embodiment, it has been found particularly advantageous to effect contact between sulfur trioxide and hydrogen fluoride at temperatures at which substantially liquid phase conditions will be maintained. In general, temperatures during such contacting should be maintained in the range of from above the normal boiling point of the saturated light hydrocarbon, i.e., the boiling point measured at atmospheric pressure, and less than about 200° F. In another embodiment of the present invention, such undesirable side reactions can be substantially eliminated by using an inert gas such as nitrogen as the stripping agent. In a preferred embodiment, a portion of the regenerated fluorosulfuric acid is recycled to the alkylation process.

DETAILED DESCRIPTION OF THE INVENTION

Figure 1:
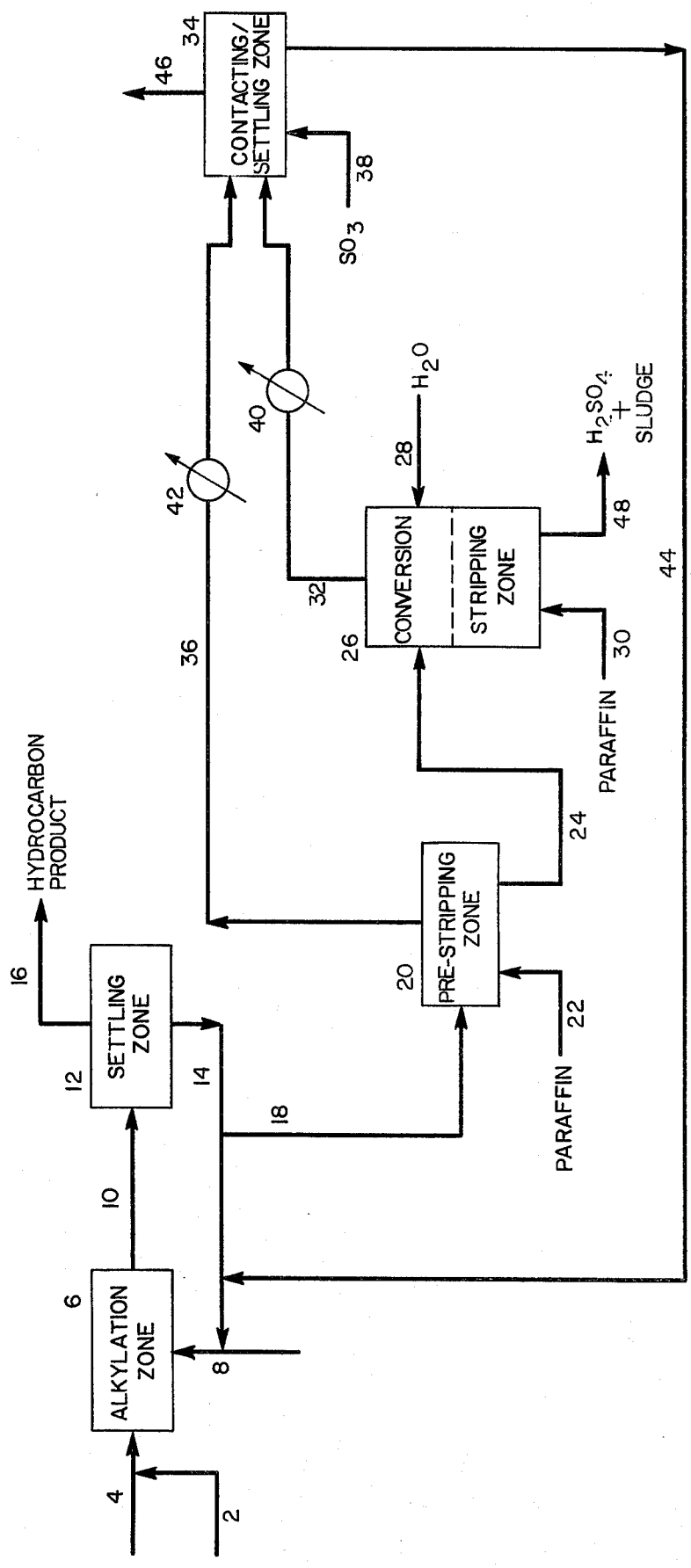
FIG. 1 is a flow diagram illustrating one embodiment of the present invention.

Having thus described the invention in general terms, reference is now made to FIG. 1 which shows an alkylation process using a catalyst system such as that described in U.S. Pat. No. 3,887,635, the disclosures of which are incorporated herein by reference. Such details are included as are necessary for a clear understanding of how the present invention may be applied in the regeneration of an alkylation catalyst comprising fluorosulfuric acid, said catalyst being at least partially deactivated. No intention is made to unduly limit the scope of the present invention to the particular configuration shown as variations obvious to those having ordinary skill in the art of alkylation and other unit processes are included within the broad scope of the present invention.

Referring now to FIG. 1, there is shown an olefin stream in line 2 which is, preferably, admixed with a paraffin stream in line 4 before introducing the combined stream into alkylation zone 6. If desired, however, the olefin and paraffin streams can be fed directly into alkylation zone 6. The olefin concentration in the feed ranges from 0.5 to 25 volume percent based on total feed and preferably below 10 volume percent. Translated into volume ratios, high volume ratios of paraffin to olefin ranging from 10:1 to 200:1 or higher are preferred, although somewhat lower ratios may be used, e.g. 3:1. Correspondingly high volume ratios of paraffin to olefin are also desired within the alkylation zone. Preferably, the paraffin/olefin ratio therein ranges from about 5:1 to 2,000:1 or higher.

Suitable olefinic reactants include $C_2$–$C_{12}$ terminal and internal monoolefins such as ethylene, propylene, isobutylene, butene-1, butene-2, the pentenes (e.g. trimethylethylene) and similar higher monoolefinic hydrocarbons of either a straight chain or a branched chain structure. Preferably, the $C_2$–$C_6$ monoolefins are used, although the highly-branched $C_7$–$C_{12}$ monoolefins may also be used. The reaction mixtures may also contain small amounts of diolefins and other hydrocarbons normally present in refinery hydrocarbon streams. Although it is desirable from an economic standpoint to use the normally gaseous olefins as reactants, normally liquid olefins may be used. Thus, reactable polymers, copolymers, interpolymers, crosspolymers, and the like, of the above-mentioned olefins, such as, for example, the diisobutylene and triisobutylene polymers, the codimer of normal butylene and isobutylene, may be employed as an olefinic reactant. Mixtures of two or more of the olefins described above can be used as the process feedstock.

$C_2$, $C_3$, $C_4$ and/or $C_5$ olefin cuts from thermal and/or catalytic cracking units; field butanes which have been subjected to prior isomerization and/or partial dehydrogenation treatment; refinery stabilizer bottoms; spent gases; normally liquid products from sulfuric acid or phosphoric acid catalyzed polymerization and copolymerization processes; and products, normally liquid in character, from thermal and/or catalytic cracking units, are all excellent feedstocks for the present alkylation process. Such feeds are preferably dried to control excess water buildup, ie. to about 5 to 15 wppm or less of water before entering the alkylation zone.

The paraffinic feedstocks that can be reacted with the olefins desirably comprise straight and/or branched chain $C_4$–$C_{10}$ paraffins such as hexane, butane and the like, and preferably, $C_4$–$C_6$ isoparaffins such as isobutane, isopentane, isohexane and the like. While open chain hydrocarbons are preferred, cycloparaffins such as methylcyclopentane may also be used.

Returning to FIG. 1, a catalyst comprising fluorosulfuric acid and one or more moderators is shown being introduced into alkylation zone 6 via line 8. Generally, the moderator contains at least one oxygen atom per molecule and includes water, aliphatic and cycloaliphatic alcohols and ethers, aliphatic, cycloaliphatic and aromatic sulfonic and carboxylic acids and their derivatives, inorganic acids and other oxygen containing organic compounds. By the term "moderator" is meant a compound which, in combination with fluorosulfuric acid, produces a catalyst system of reduced acidity vis-a-vis the fluorosulfuric acid, and thereby decreases the probability of undesirable competing side reactions which have a detrimental effect on product quality, while increasing catalyst selectivity to desirable highly branched paraffinic products, thus resulting in higher quality alkylate product than would otherwise be achieved. Various moderators that can be employed in the present catalyst system are shown at column 2, lines 38–67, column 3, lines 16–68 and column 4, lines 1–23 of U.S. Pat. No. 3,887,635.

Preferred catalyst moderators contain either a hydroxy group such as alcohols or a hydroxy group precursor, such as ethers, which, it is speculated, can potentially cleave to form alcohols under the acidic conditions of the subject invention. Of these, the more preferred moderators are the alcohols and water, the most preferred being water. It is noted that the catalyst moderator and the fluorosulfuric acid can be premixed prior to introduction into the reactor, thereby forming the catalyst system. The catalyst may also be formed in situ.

The exact mechanism by which the moderator compounds effectuate increase catalyst selectivity while reducing competitive side reactions is not known. However, the active catalyst species employed herein is postulated to be an equilibrium mixture comprising several components. By way of illustration, it is speculated that the addition of water to fluorosulfuric acid, results in initial dissociation of the strong acid followed by hydrolysis:

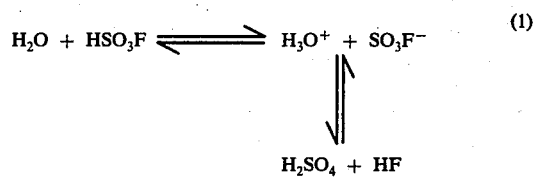

The equilibrium is believed to lie towards the right and, therefore, little, if any, free water should exist in the strong acid system. Similar mechanisms can be postulated for other moderators such as alcohols and ethers.

By the very nature of the postulated mechanism, it is clear that the manner in which the active catalytic system is formed is immaterial. Thus, in the above example, mixing HF and $H_2SO_4$ in equal molar amounts should result in the same catalyst system as would be obtained by mixing water with $HSO_3F$. The active catalyst system may also be formed by mixing HF, $H_2SO_4$ and $HSO_3F$ or HF, $SO_3$ and $H_2O$ in appropriate amounts. Hence, when the catalyst system is described as "being formed from" a strong acid and a moderator, it is not meant to be limited to any one catalyst formation mode; rather, this description is used merely for convenience in providing a simple definition of the active catalyst system.

The amount of moderator used in forming the catalyst system is an important variable in the production of high quality alkylate. The desired amounts of moderator will vary dependent, in part, on the alkylation temperature. Thus, for example, at temperatures between about 0° to 40° F., useful amounts of moderator can range between about 5 and 45 mole % based on acid. In some instance, however, it may be desirable to use somewhat lower or higher amount of moderator, e.g. 50 mole % based on acid, where, for example, different catalyst activity or selectivity is desired.

At high alkylation temperatures, e.g. between about 40° and 100° F., increased amount of moderator may be desirable due to the increased strong acid activity. Thus, an amount of moderator ranging between about 50 and 100 mole % based on acid may be used at these higher temperatures. In fact, under appropriate conditions, these higher amounts of moderator may also be utilized at the lower temperatures disclosed hereinabove, if desired. A preferred catalyst is one formed from fluorosulfuric acid and from about 5 to 100 mole %, based on acid, of (1) water, (2) $C_1$-$C_7$ saturated aliphatic monohydroxy alcohol or (3) a mixture of water and said alcohol.

Although the broad concentration ranges are generally independent of the type of moderator used, the preferred or optimal range will vary depending on the structure of the moderator, the reaction temperature, the concentration and nature of the olefin in the feed, the amount of organic sludge present, and the olefin space velocity and the like.

In addition to being used in classical alkylation processes as hereinabove described, the catalyst system employed herein may also be used in self-alkylation processes, which are also known as hydrogen transfer alkylation processes. The $C_4$-$C_{16}$ branched chain olefins and $C_4$-$C_8$ isoparaffins are preferred reactants. The process is generally conducted in the liquid phase whereby the isoparaffin is dimerized and the olefin is saturated to the corresponding paraffin, thus producing an alkylate-type product of high quality. Self-alkylation processes are generally described in U.S. Pat. No. 3,150,204. Undesired side reactions are minimized using these catalyst systems, thereby providing high yields of the desired products.

In general the amount of olefin contacted with the catalyst can range from about 0.05 to 1000 volumes of olefin per hour per volume of catalyst inventory in the reactor (V/V/Hr.), i.e. olefin space velocity. Preferably, the olefin space velocity ranges from about 0.05 to 10.0 V/V/Hr., and still more preferably from about 0.05 to 1.0 V/V/Hr., e.g. 0.1 V/V/Hr. The volume % of total catalyst in the reaction mixture or emulsion (when liquid phase operations are used) in the alkylation zone can range from about 30 to 80 volume % based on total reaction mixture and preferably from about 50 to 70 volume %. The isoparaffin concentration, including alkylate, in the hydrocarbon phase (in a liquid phase process) can range from about 40 to about 100 volume % based on the total volume of the hydrocarbon phase and preferably from 50 to 90 volume %. Such isoparaffin concentrations can be maintained by recycling unreacted isoparaffin to the alkylation zone.

The process may be carried out either as a batch or continuous type of operation, although it is preferred for economic reasons to carry out the process continuously. It has been generally established that in alkylation processes, the more intimate the contact between the feedstock and the catalyst the better the yield of saturated product obtained. With this in mind, the present process, when operated in either a batch or in a continuous manner, is characterized by the use of vigorous mechanical stirring or shaking of the reactants with the catalyst.

In continuous operations, as that of the embodiment shown in FIG. 1, the reactants may be maintained at sufficient pressures and temperatures to maintain them substantially in the liquid state and then continuously forced through dispersion devices into the alkylation zone. The dispersion devices may be jets, porous thimbles and the like. The reactants are subsequently mixed with the catalyst in alkylation zone 6 by conventional mixing means (not shown) such as mechanical agitators and the like. While the alkylation reaction can be carried out at a temperature within the range of from about $-80°$ to $+100°$ F., fairly low reaction temperatures, preferably within the range of from about $-80°$ to $+70°$ F., and most preferably within the range of from about $-20°$ to about $+40°$ F., are usually employed. Where the reaction is carried out at temperatures about $+10°$ F., or higher it is necessary that the reaction be conducted under superatmospheric pressure, if the reactants and/or the catalyst are to be maintained substantially in a liquid state. Typically, the alkylation reaction is conducted at pressures varying from about atmospheric to about 300 psia.

In general it is preferable to employ pressures sufficiently high to maintain the reactants in the liquid phase although a vapor phase operation is also contemplated. Autorefrigerated reactors and the like may be employed to maintain liquid phase operation.

After allowing sufficient residence time for the reaction to progress, typically on the order from about one minute to one hour or more, the reaction mixture which contains hydrocarbon and deactivated or partially deactivated catalyst (often referred to as the "emulsion mixture") is withdrawn from the alkylation zone 6 via line 10 and passed into a settling zone 12. The reaction mixture will separate in zone 12 into a heavy acid phase containing the fluorosulfuric acid, sulfuric acid, hydrogen fluoride, and moderator (assumed to be water for the purpose of illustration in the following discussion), as well as organic sludge formed during said alkylation, and a hydrocarbon phase containing the alkylate product along with smaller amounts of fluorosulfuric acid, hydrogen fluoride and water which are dispersed and/or dissolved therein. The acid phase is withdrawn from settling zone 12 via line 14 and at least a portion thereof can be recycled to alkylation zone 6 via line 8 or charged to another alkylation zone, if desired. The hydrocarbon phase is withdrawn from settling zone 12 via line 16.

The present invention will now be illustrated with reference to removing a portion of the fluorosulfuric acid from the deactivated or partially deactivated catalyst prior to contacting same with water (i.e. prestripping), as is disclosed in application Ser. No. 772,641, filed on the same date herewith. However, it should be clearly understood that while prestripping is a preferred embodiment of the present invention, this invention is equally applicable to regeneration processes which do not include prestripping, such as those disclosed in U.S. Pat. Nos. 3,766,293 and 3,976,759.

Referring again to FIG. 1, a purge stream of the heavy acid phase is shown being withdrawn from line 14 and being passed via line 18 into prestripping zone 20 wherein said purge stream is intimately contacted with a stripping agent introduced via line 22. Suitable stripping agents are saturated light hydrocarbons, inert gases and mixtures thereof. Suitable light hydrocarbons include paraffins, preferably $C_3$-$C_6$ paraffins, more preferably $C_4$ paraffins. Normal butane is the preferred $C_4$ paraffin. Nitrogen is the preferred inert gas. However, for the purpose of the following discussion, the stripping agent will be assumed to be a paraffin.

As a result of said contacting, a portion, preferably a major portion, of both the hydrofluoric acid and the fluorosulfuric acid are stripped from said purge stream, thereby forming a gas phase containing stripping agent (e.g. paraffin), fluorosulfuric acid and hydrogen fluoride and a liquid phase containing fluorosulfuric acid, organic sludge and sulfuric acid as well as traces of hydrogen fluoride. The amount of stripping agent employed is that required to remove the desired amount of fluorosulfuric acid. It should be pointed out that hydrofluoric acid and sulfuric acid are present in streams 14 and 18 because the fluorosulfuric acid is partially hydrolyzed when contacted with the moderator, e.g. water. If no moderator is employed, small amounts of water are normally introduced into the alkylation zone (e.g. with the feed) such that said partial hydrolysis will occur. Be that as it may, however, the present regeneration process is also applicable to a fluorosulfuric acid catalyst that has not been hydrolyzed.

The liquid phase then passes from prestripping zone 20 via line 24 into the middle portion of conversion/stripping zone 26 wherein it is contacted with water injected via line 28 in an amount sufficient to convert the fluorosulfuric acid to free hydrogen fluoride and sulfuric acid according to the reaction:

$$H_2O + HSO_3F \rightleftharpoons H_2SO_4 + HF + \text{Heat} \quad (2)$$

In one embodiment of the invention, it may be desirable to add up to a mole of water in excess of the stoichiometric amount required. Preferably, less than about 0.5 mole excess water is used. The resulting stream of water, hydrogen fluoride, sulfuric acid and organic sludge is then passed into the lower portion of zone 26 and intimately contacted therein with the stripping agent introduced via line 30, thereby stripping the hydrogen fluoride from said stream and forming a gaseous phase containing hydrogen fluoride and stripping agent.

The particular temperatures and pressures employed in pre-stripping zone 20 and in conversion/stripping zone 26 are determined in general, by economic factors such as cost or availability of stripping agent and the like. The cost of $SO_3$ is an added consideration for zone 20. Normally zones 20 and 26 should be operated at temperatures above that at which the partial pressure of fluorosulfuric acid and hydrogen fluoride, respectively, become sufficiently low such that uneconomical amounts of stripping agent are required. It is also desirable to operate zones 20 and 26 at as high a temperature as possible because better stripping is obtained and less stripping agent is required. However, we have discovered that undersirable side reactions between the fluorosulfuric acid and acidic components in the catalyst (e.g. $H_2SO_4$ and the like) and the hydrocarbon stripping agent, as well as the organic sludge, become excessive at elevated temperatures, i.e. temperatures above about 250° F. Such reactions result in the formation of a polymer-like material, e.g. coke, that could "plug" the system. Thus, while elevated temperatures would normally be preferred, we have discovered that the temperature in both zones should be maintained below that at which undesirable reactions between the acid and the light hydrocarbon stripping agent become excessive. This corresponds to less than 70%, preferably less than 40%, more preferably less than 25%, most preferably less than 10%, of the sulfur in the acid components of the partially deactivated catalyst being reduced. Typically, the temperature of conversion/stripping zone 26 should be maintained in the range of from above about 120° to about 250° F., preferably in the range of from about 130° to about 210° F., and more preferably in the range of from about 140° to 170° F. Total pressure of zones 20 and 26 can also vary according to the economic factors mentioned above. In general, however, the total pressure will range from about atmospheric pressure to about 170 psia, preferably from about atmospheric to about 120 psia, and more preferably from about atmospheric to about 90 psia.

The gas phase from zone 26 is passed via line 32 into contacting/settling zone 34 as is the gas phase from pre-stripping zone 20 via line 36, wherein the hydrogen fluoride present in each stream is reacted with at least a stoichiometric amount of sulfur trioxide, based on hydrogen fluoride, which is introduced via line 38 such that at least a portion, preferably substantially all of the hydrogen fluoride present is converted to fluorosulfuric acid under substantially liquid phase conditions according to the following reaction:

$$HF + SO_3 \rightarrow HFSO_3 + \text{heat} \quad (3)$$

The $SO_3$ may be employed in any convenient form such as, for example, stabilized or unstabilized $SO_3$, oleum and the like. Thus, $SO_3$ is meant to include $SO_3$ from any of the aforementioned sources. Also, as discussed below, the gas phases from zones 20 and 26 are cooled to a temperature sufficient to form a mixed phase comprising at least a liquid phase containing hydrogen fluoride, i.e., a mixed phase containing said liquid phase and a gas phase containing stripping agent. Fluorosulfuric acid and hydrogen fluoride may also be present in the vapor or liquid phase depending upon the amount of water employed in reaction (2). A major portion of the liquid and gas phase will contain HF and stripping agent, respectively. According to the present invention, it has been discovered that contacting/settling zone 34 must be maintained at reduced temperatures relative to the pre-stripping zone 20 and conversion/stripping zone 26. While not wishing to be bound by any particular theory, it is believed that since the sulfur in sulfur trioxide is in the +6 valence state (and a stronger oxidizing agent than that employed in zones 20 and 26), the sulfur can oxidize hydrocarbon (e.g. a paraffin stripping agent) to form water and carbon monoxide according to the following reaction (which is illustrated for butane):

$$9SO_3 + C_4H_{10} \rightarrow 9SO_2 + 5H_2O + 4CO \quad (4)$$

In addition, due to the availability (i.e. concentration) of free sulfur trioxide (a strong oxidizing agent) in contacting/settling zone 34, it has been found necessary to effect reaction (3) at reduced temperature conditions. Broadly speaking, the temperature of zone 34 should be maintained in the range of from about the normal boiling point of the stripping agent to less than about 200° F., preferably less than 110° F., but at a temperature at which at least a portion of the hydrogen fluoride present in gas phases 32 and 36 will be in the liquid phase. Preferably, the temperature should be maintained in the range of from about 10° to about 100° F. and more preferably from about 10° to about 70° F. Cooling the gas phases in lines 32 and 36 to within the range of temperatures noted above may be by any suitable means including, for example as shown in the Figure, condensation zones 40 and 42, respectively. However, other cooling configurations may be employed. For example, if desired, both gas phases could be cooled in a single condensation zone or the cooling could be effected within zone 34. It may be desirable to cool the gas phases in lines 32 and 36 to a level sufficient to maintain the desired temperature in zone 34, i.e. to offset the heat evolved by reaction (3). The pressure of contacting/stripping zone 34 is not critical and will, in general, be within the range of that specified for stripping zones 20 and 26.

Following the contacting to effect reaction (3), the mixture within zone 34 is separated into a liquid phase comprising regenerated fluorosulfuric acid and water (at least a portion of which may be from reaction (4) and a gas phase comprising stripping agent. Preferably, substantially all of the fluorosulfuric acid is in the liquid phase, such that the gas phase contains only trace amounts of said acid, e.g. typically less than 500 ppm.

Regenerated fluorosulfuric acid, which may contain small amounts of water, is withdrawn from contacting/stripping zone 34 via line 44 and at least a portion thereof is combined with the recycle stream 14 for return to alkylation zone 6 via line 8. A phase containing stripping agent is removed from contacting/separation zone 34 via line 46, said phase being either gaseous or liquid depending upon the temperature and pressure conditions employed in zone 34. If desired, at least a portion of the stripping agent phase may be recycled to conversion/stripping zone 26, to pre-stripping zone 20 and contacting/stripping zone 34 for temperature control purposes or be used as part of the stripping agent in zones 20 and 26. Additional hydrocarbon stripping agent can be introduced into said stripping zones if desired. Sulfuric acid and the sludge formed during the alkylation process can be removed from the bottom of conversion/stripping zone 26 via line 48 and sent to sulfuric acid regeneration (not shown) for sludge removal and reconcentration, or it can be discarded. Alternately, the sulfuric acid sludge stream can be employed for removing dissolved and/or dispersed fluorosulfuric acid from hydrocarbon phase 16.

The stripping zones and conversion tower are conventional equipment sutiable for gas-liquid or liquid-liquid contacting and are available from various equipment vendors. As such, they do not form a part of this invention. However, the present invention enables the use of less expensive materials of construction than normally required, i.e., materials other than Hasteloy.

As previously noted, hydrocarbon phase 16 contains dissolved and/or dispersed fluorosulfuric acid, water, hydrogen fluoride from partial dissociation of the acid, the other acidic materials such as sulfur dioxide, etc. If desired, the acid materials which are dissolved and/or dispersed in hydrocarbon phase 16 can be effectively removed by scrubbing said hydrocarbon phase with sulfuric acid. The sulfuric acid is preferably concentrated, being 98.0 to 100% $H_2SO_4$, but somewhat more dilute acid (95–97.9%) can also be used without substantial detriment to the efficiency of the process. The manner of scrubbing may be by any conventional means, such as by passing the sulfuric acid and hydrocarbons through a mixing orifice, a countercurrent contacting tower or by injectng them into a centrifugal pump, etc., as long as intimate contact between the hydrocarbon phase and the sulfuric acid is attained. The ratio of acid to hydrocarbon is not critical, but can vary from about 5 to 95% of the hydrocarbon stream. The temperature for scrubbing generally ranges from about 20° to 100° F. but must be above the freezing point of sulfuric acid. The pressure may be any pressure from atmospheric to about 500 psig. The resulting phases are settled after contacting. The hydrocarbon phase containing alkylate product may undergo further treatment to remove trace amounts of any acid materials present therein. Fluorosulfuric acid present in the sulfuric acid phase thus settled may be removed therefrom by introducing the acid phase into the regeneration process described above, e.g. into pre-stripping zone 20 or preferably, directly into conversion/stripping zone 26.

The following example is presented to further illustrate the present invention and is not intended to unduly restrict the limits of the claims appended hereto:

EXAMPLE

Effect of Temperature upon Sulfate Sulfur and Fluorosulfate Content in $HSO_3F$ Regeneration Various runs were made contacting spent fluorosulfuric catalyst with either normal butane or isobutane. In a typical run, 120 cc's of spent fluorosulfuric acid alkylation catalyst were charged to a one liter autoclave along with 500 cc's of the butane. Then the autoclave was sealed, heated quickly to the specified temperature and held there for one hour. Then the heat was shut off, the autoclave was cooled rapidly, and the acid phase sampled for analysis. The sulfur content was determined by barium sulfate precipitation and includes both sulfate sulfur and fluorosulfate sulfur which was hydrolyzed to sulfate in the analysis. The results obtained are shown in FIG. 2.

Figure 2:
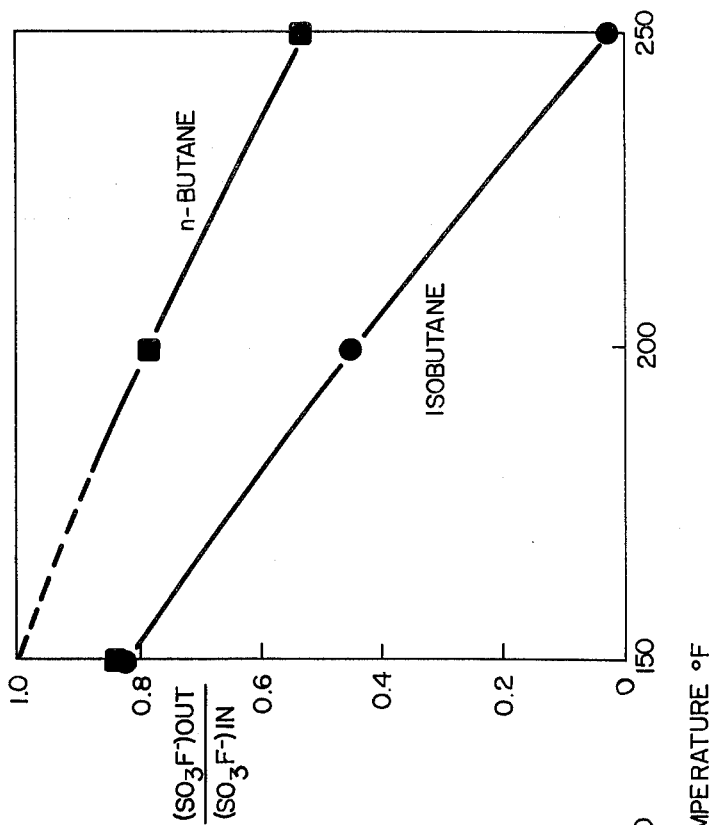
FIG. 2 shows the effect of temperature upon the sulfate ion concentration in $HSO_3F$ regeneration.

FIG. 2 shows the ratio of the sulfur in the +6 oxidation state in the final product to that in the charged catalyst. As shown, at 150° F., less than 10% of the sulfur was reduced from the sulfate to the sulfite form, i.e., the $SO_4=$ out divided by the $SO_4=$ in was equal to or greater than 0.9. At the other extreme, 250° F., about 70% of the sulfur was reduced with isobutane and 40% with n-butane. These data show that the extent of the oxidation-reduction reactions increases rapidly as regeneration temperature is increased.

Figure 3:
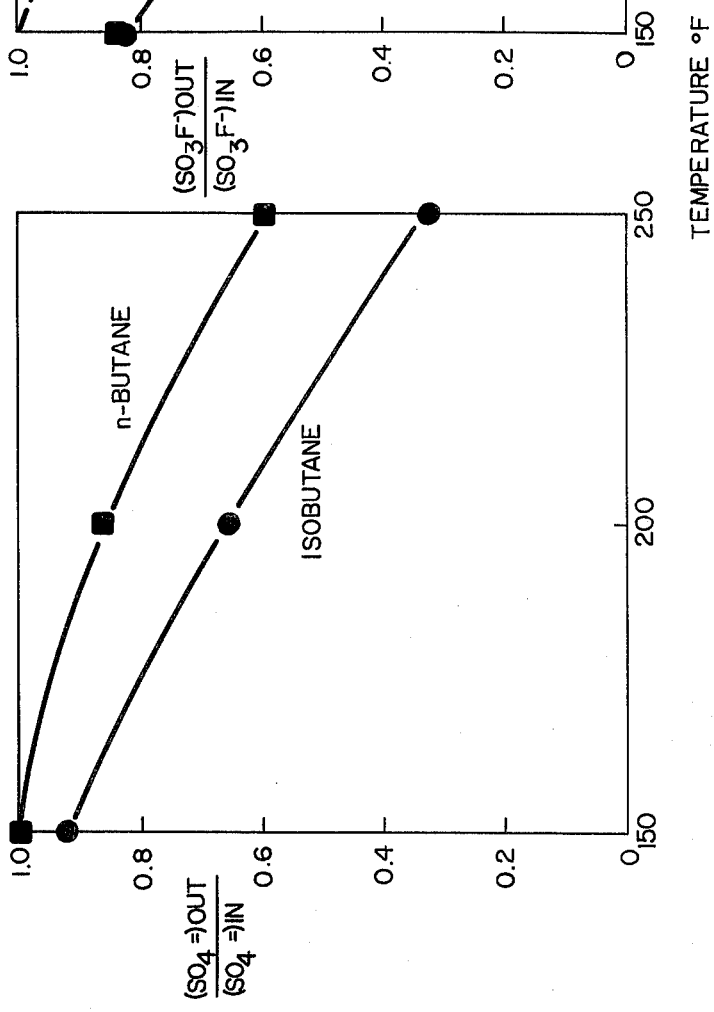
FIG. 3 shows the effect of temperature upon the fluorosulfate ion concentration in $HSO_3F$ regeneration.

FIG. 3 shows data from the same experiments for the fluorosulfate ion in the product divided by the fluorosulfate ion content in the charge acid. The fluorosulfate concentration was determined by precipitation with nitron reagent. The data show the same general trends as did the sulfate data.

It should be pointed out that the level of activity at which the fluorosulfuric acid catalyst should be regenerated is not only a matter of ability to catalyze the alkylation reaction, but also a matter of economics. For example, it may be desirable to regenerate a mildly deactivated catalyst to essentially fresh catalyst activity rather than allow the catalyst to be reduced to a much lower level of activity and be regenerated to fresh or to less than fresh activity. Thus, as used herein, the term "regeneration" or "regenerated" means recovering a fluorosulfuric acid catalyst that possesses a greater activity for alkylation than that possessed by the deactivated or partially deactivated catalyst. It should be understood that the regeneration process of the present invention is applicable to catalysts such as those defined above which have lost some degree of activity and that the regeneration may only partially restore the lost activity.

Although the present regeneration process has been discussed with reference to the alkylation process and catalyst described in U.S. Pat. No. 3,887,635, it should be understood that it is applicable to any alkylation process that employs fluorosulfuric acid (see for example U.S. Pat. Nos. 3,922,319 and 3,928,487, the disclosures of which are incorporated herein by reference), including those processes that form fluorosulfuric acid from a strong acid and a moderator, e.g. mixing sulfuric acid and hydrofluoric acid in appropriate amounts, alone or in the presence of HSO₃F (see for example U.S. Pat. No. 3,956,418).

What is claimed is:

1. In an alkylation process which comprises:
   (a) contacting an olefin with a paraffin in an alkylation zone under alkylation conditions and with a catalyst comprising fluorosulfuric acid to form a reaction mixture of fluorosulfuric acid catalyst phase containing an organic sludge formed during said process and a hydrocarbon phase containing alkylate product;
   (b) separating said hydrocarbon phase containing alkylate product from said fluorosulfuric acid catalyst phase, the improvement which comprises regenerating said acid catalyst phase according to the following steps:
   (c) stripping a portion of the fluorosulfuric acid from the acid catalyst phase separated in step (b) with a paraffin to form a stripped acid phase containing fluorosulfuric acid and said organic sludge and a gaseous phase containing paraffin and fluorosulfuric acid;
   (d) contacting said stripped acid phase formed in step (c) with water to form an acid-water mixture, thereby converting at least a portion of the fluorosulfuric acid contained therein to hydrogen fluoride and sulfuric acid;
   (e) stripping at least a portion of the hydrogen fluoride from said acid-water mixture formed in step (d) with a paraffin to form a gaseous phase comprising hydrogen fluoride and paraffin and a liquid phase comprising sulfuric acid and organic sludge, the stripping of step (c) and step (e) being effected at a temperature between from above 120° to about 250° F;
   (f) cooling the gaseous phases formed in step (c) and step (e) to a temperature ranging from about the normal boiling point of said paraffin to less than 110° F to form a liquid-vapor mixture comprising a liquid phase containing fluorosulfuric acid and hydrogen fluoride and a vapor phase containing paraffin;
   (g) treating the liquid-vapor mixture formed in step (f) in a contacting zone with at least a stoichiometric amount of sulfur trioxide based on hydrogen fluoride, at a temperature ranging from about the normal boiling point of said paraffin to less than 110° F, to convert the hydrogen fluoride present therein to fluorosulfuric acid, thereby forming a liquid phase of regenerated fluorosulfuric acid and a gas phase containing predominantly paraffin.

2. The process of claim 1 wherein said regenerated fluorosulfuric acid is recycled to said alkylation zone in step (a).

3. The process of claim 1 wherein the alkylation catalyst includes a moderator in an amount of about 5 to 100 mole %, based on acid, of (1) water, (2) a C₁–C₇ saturated aliphatic monohydroxy alcohol, or (3) a mixture of water and said alcohol.

4. The process of claim 3 wherein said moderator is water.

5. The process of claim 1 wherein the paraffin used for stripping is a C₄ paraffin.

6. The process of claim 5 wherein the C₄ paraffin is n-butane.

7. The process of claim 1 wherein the temperature in step (f) and step (g) ranges from about 10° to about 100° F.

8. The process of claim 1 wherein the temperature of step (f) and step (g) ranges from about 10° to about 70° F.

9. The process of claim 1 wherein the acid catalyst phase of step (b) contains HF.

10. In an alkylation process which comprises:
    (a) contacting an olefin with a paraffin in an alkylation zone under alkylation conditions and with a catalyst comprising fluorosulfuric acid to form a reaction mixture of fluorosulfuric acid catalyst phase containing an organic sludge formed during said process and a hydrocarbon phase containing alkylate product;
    (b) separating said hydrocarbon phase containing alkylate product from said fluorosulfuric acid catalyst phase, said hydrocarbon phase containing a portion of the fluorosulfuric acid;
    (c) washing said hydrocarbon phase with an acid comprising sulfuric acid thereby removing at least a portion of the fluorosulfuric acid from said hydrocarbon phase and separating a sulfuric acid phase containing said fluorosulfuric acid from said hydrocarbon phase containing the alkylate product, the improvement which comprises regenerating said acid catalyst phase according to the following steps:
    (d) stripping a portion of the fluorosulfuric acid from the acid catalyst phase separated in step (b) with a paraffin to form a stripped acid phase containing fluorosulfuric acid and organic sludge and a gaseous phase containing said paraffin and fluorosulfuric acid;
    (e) contacting said stripped acid phase formed in step (d) and the sulfuric acid phase separated in step (c) with water to form an acid-water mixture, thereby converting at least a portion of the fluorosulfuric acid contained therein to hydrogen fluoride and sulfuric acid;
    (f) stripping at least a portion of the hydrogen fluoride from said acid-water mixture formed in step (e) with a paraffin to form a gaseous phase comprising hydrogen fluoride and paraffin and a liquid phase comprising sulfuric acid and organic sludge, the stripping of step (d) and step (f) being effected at a temperature from above 120° to about 250° F;
    (g) cooling the gaseous phases formed in step (d) and step (f) to a temperature ranging from about the normal boiling point of said paraffin to less than 110° F to form a liquid-vapor mixture comprising a liquid phase containing fluorosulfuric acid and hydrogen fluoride and a vapor phase containing paraffin;
    (h) treating the liquid-vapor mixture formed in step (g) in a contacting zone with at least a stoichiometric amount of sulfur trioxide based on hydrogen fluoride, at a temperature ranging from about the normal boiling point of said paraffin to less than 110° F to convert the hydrogen present therein to fluorosulfuric acid, thereby forming a liquid phase of regenerated fluorosulfuric acid and a gas phase containing predominantly paraffin.

11. The process of claim 10 wherein the catalyst includes a moderator in an amount of from about 5 to 100 mole %, based on acid, of (1) water, (2) a C₁–C₇ saturated aliphatic monohydroxy alcohol or (3) a mixture of water and said alcohol.

12. The process of claim 10 wherein the alkylation catalyst includes water as a moderator.

13. The process of claim 10 wherein the acid catalyst phase of step (b) contains HG.

14. The process of claim 10 wherein the paraffin used for stripping is a $C_4$ paraffin.

15. The process of claim 10 wherein the liquid phase comprising sulfuric acid and organic sludge in step (f) is employed to wash the hydrocarbon phase in step (c).

16. The process of claim 10 wherein the temperature in step (g) and step (h) ranges from about 10° to about 100° F.

17. The process of claim 10 wherein the temperature of step (g) and step (h) ranges from about 10° to about 70° F.

18. In an alkylation process which comprises:
    (a) contacting an olefin with a paraffin in an alkylation zone under alkylation conditions and with a catalyst comprising fluorosulfuric acid to form a reaction mixture of fluorosulfuric acid catalyst phase containing an organic sludge formed during said process and a hydrocarbon phase containing alkylate product;
    (b) separating said hydrocarbon phase containing alkylate product from said fluorosulfuric acid catalyst phase, the improvement which comprises regenerating said acid catalyst phase according to the following steps:
    (c) contacting at least a portion of the fluorosulfuric acid phase separated in step (b) with water to form an acid-water mixture, thereby converting at least a portion of the fluorosulfuric acid contained therein to hydrogen fluoride and sulfuric acid;
    (d) stripping at least a portion of the hydrogen fluoride from said acid-water mixture formed in step (c) with a paraffin to form a gaseous phase comprising hydrogen fluoride and paraffin and a liquid phase comprising sulfuric acid and organic sludge, said stripping being effected at a temperature from above 120° to about 250° F;
    (e) cooling the gaseous phase formed in step (d) to a temperature ranging from about the normal boiling point of said paraffin to less than 110° F to form a liquid-vapor mixture comprising a liquid phase containing fluorosulfuric acid and hydrogen fluoride and a vapor phase containing paraffin;
    (f) treating the liquid-vapor mixture formed in step (e) in a contacting zone with at least a stoichiometric amount of sulfur trioxide based on hydrogen fluoride, at a temperature ranging from about the normal boiling point of said paraffin to less than 110° F to convert the hydrogen fluoride present therein to fluorosulfuric acid, thereby forming a liquid phase of regenerated fluorosulfuric acid and a gas phase containing predominantly paraffin.

19. The process of claim 18 wherein the hydrocarbon phase separated in step (b) is washed with an acid comprising sulfuric acid to remove at least a portion of the fluorosulfuric acid from said hydrocarbon phase, thereby forming a sulfuric acid phase containing said fluorosulfuric acid and said hydrocarbon phase containing the alkylate product, and adding said sulfuric acid phase containing said fluorosulfuric acid to said fluorosulfuric acid catalyst phase separated in step (b) to regenerate the fluorosulfuric acid present in said sulfuric acid phase.

20. The process of claim 18 wherein the temperature in step (e) and step (f) ranges from about 10° to about 100° F.

21. The process of claim 18 wherein the catalyst includes a moderator in an amount of from about 5 to 100 mole %, based on acid, of (1) water, (2) a $C_1$–$C_7$ saturated aliphatic monohydroxy alcohol, or (3) a mixture of water and said alcohol.

22. The process of claim 18 wherein the paraffin used for stripping is a $C_4$ paraffin.

* * * * *